(12) United States Patent
Papangelou et al.

(10) Patent No.: US 7,943,677 B2
(45) Date of Patent: May 17, 2011

(54) METHOD OF PRODUCING INTERCONNECTED VOLUMETRIC POROSITY IN MATERIALS

(75) Inventors: Christopher G. Papangelou, Dunedin, FL (US); Wesley M. Johnson, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 12/106,471

(22) Filed: Apr. 21, 2008

(65) Prior Publication Data

US 2008/0234401 A1 Sep. 25, 2008

Related U.S. Application Data

(63) Continuation of application No. PCT/US2006/041571, filed on Oct. 23, 2006.

(60) Provisional application No. 60/729,411, filed on Oct. 21, 2005.

(51) Int. Cl.
- *C08J 9/26* (2006.01)
- *C08J 9/28* (2006.01)
- *B29C 67/20* (2006.01)
- *A61F 2/28* (2006.01)

(52) U.S. Cl. ............... 521/63; 623/16.11; 264/49

(58) Field of Classification Search ............ 264/49; 521/63; 623/16.11
See application file for complete search history.

(56) References Cited

U.S. PATENT DOCUMENTS

| | | | |
|---|---|---|---|
| 3,893,196 A * | 7/1975 | Hochman | 424/422 |
| 4,078,129 A * | 3/1978 | Yamagata et al. | 528/488 |
| 4,892,544 A * | 1/1990 | Frisch | 128/898 |
| 4,906,423 A * | 3/1990 | Frisch | 264/48 |
| 5,021,462 A | 6/1991 | Elmes et al. | |
| 5,958,314 A | 9/1999 | Draenert | |
| 6,187,329 B1 | 2/2001 | Agrawal et al. | |
| 6,255,359 B1 | 7/2001 | Agrawal et al. | |
| 6,905,516 B1 | 6/2005 | Lemaitre et al. | |
| 7,575,759 B2 | 8/2009 | Murphy et al. | |
| 2003/0152606 A1 | 8/2003 | Gerber | |
| 2004/0119181 A1 * | 6/2004 | Descamps et al. | 264/40.1 |
| 2005/0163861 A1 | 7/2005 | Epple et al. | |

FOREIGN PATENT DOCUMENTS

| | | |
|---|---|---|
| EP | 0988839 A3 | 4/2000 |
| EP | 00914072 B1 | 5/2004 |
| EP | 01516635 A1 | 3/2005 |
| EP | 01520593 A1 | 4/2005 |
| GB | 02354519 | 3/2001 |
| WO | 02/081408 A1 | 10/2002 |
| WO | 2007/086964 A3 | 8/2007 |

OTHER PUBLICATIONS

Cyster, L. A.; Grant, D. M.; Howdle, S. M.; Rose, F. R. A. J.; Irvine, D. J.; Freeman, D.; Scotchford, C. A.; Shakesheff, K. M. 2005. "The influence of dispersant concentration on the pore morphology of hydroxyapatite ceramics for bone tissue engineering." Biomaterials. vol. 26. No. 7. Mar. 2005. pp. 697-702.

Liu, Xiaohua; MA, Peter X. 2004. "Polymeric scaffolds for bone tissue engineering." Annals of Biomedical Engineering.vol. 32. No. 3. Mar. 2004. pp. 477-486.

Laurencin, Cato T.; Attawia, Mohamed; Borden, Mark; Khan, Yusuf. 2002. "Tissue engineered microsphere-based matrices for bone repair: Design and evaluation." Biomaterials. vol. 23. No. 2. Jan. 2002. pp. 551-559.

Laurencin, C. T.; Botchwey, E. A.; Levine, E. M.; Pollack, S. R. 2001. "Bone tissue engineering in a rotating bioreactor using a microcarrier matrix system." Journal of Biomedical Materials Research. vol. 55. No. 2. May 2001. pp. 242-253.

Hutmacher, Dietmar W. 2000. "Scaffolds in tissue engineering bone and cartilage." Biomaterials. vol. 21. No. 24. Dec. 2000. pp. 2529-2543.

Sepulveda, P.; Binner, J. G. P.; Bressiani, J. C. ; Higa, O. Z.; Rogero, S. O. 2000. "Production of porous hydroxyapatite by the gel-casting of foams and cytotoxic evaluation." Journal of Biomedical Materials Research. vol. 50. No. 1. Apr. 2000. pp. 27-34.

Li, H.; Lin, K.; Chang, J. 2005. "Preparation of macroporous polymer scaffolds using calcined cancellous bone as a template." Journal of Biomaterials Science. Polymer Ed. vol. 16 No. 5. 2005. pp. 575-584.

Gross, K. A.; Rodriguez-Lorenzo, L. M. 2004. "Biodegradable composite scaffolds with an interconnected sperical network for bone tissue engineering." Biomaterials. vol. 25. No. 20. 2004. pp. 4955-4962.

Almirall, A.; Larrecq, G.; Delgado, J. A.; Martinez, S.; Planell, J. A.; Ginebra, M. P. 2004. "Fabrication of low temperature macroporous hydroxyapatite scaffolds by foaming and hydrolysis of an (alpha)-TCP paste." Biomaterials. vol. 25. No. 17. 2004. pp. 3671-3680.

Padilla, S.; Roman, J.; Vallet-Regi, M. 2002. "Synthesis of porous hydroxyapatites by combination of gelcasting and foams burn out methods." Journal of Materials Science: Materials in Medicine. vol. 13. No. 12. 2002. pp. 1193-1197.

(Continued)

*Primary Examiner* — Mark Eashoo
*Assistant Examiner* — Liam J Heincer
(74) *Attorney, Agent, or Firm* — Michele L. Lawson; Smith & Hopen, P.A.

(57) ABSTRACT

A method to create interconnected porosity in materials that can be poured or injected into a cast. The process allows the arrangement of interconnected volumetric porosity to be directed in materials that are poured or injected into a cast. This process allows a manufacturer to tailor porosity with any size, shape, and configuration with the dissolvable material used to create the pores. This procedure can be applied to medical materials to direct bone growth or implant attachment. These resulting porous materials can include, but is not limited to short fiber reinforced epoxy or epoxy.

27 Claims, 4 Drawing Sheets

OTHER PUBLICATIONS

Zhang, R.; MA, P. X. 1999. "Poly((alpha)-hydroxyl acids)/hydroxyapatite porous composites for bone-tissue engineering. I. Preparation and morphology." Journal of Biomedical Materials Research. vol. 44. No. 4 pp 446-455.

Ramay, Hassna Rehman; Zhang, Miqin. 2003. "Preparation of porous hydroxyapatite scaffolds by combination of the gel-casting and polymer sponge methods." Biomaterials. vol. 24. No. 19. Aug. 2003. pp. 3293-3302.

Hu, Yunhua; Grainger, David W; Winn, Shelley R; Hollinger, Jeffrey O. 2002. "Fabrication of poly (alpha-hydroxy acid) foam scaffolds using multiple solvent systems." J Biomed Mater Res. vol. 59 No. 3. Mar. 2002. pp. 563-572.

Fisher, J P; Holland, T A; Dean, D; Engl, P S; Mikos, A G. 2001. "Synthesis and properties of photocross-linked poly(propylene fumarate) scaffolds." J Biomater Sci Polym Ed. vol. 12. No. 6. 2001. pp. 673-687.

Charles M. Lofton, Claudia B. Milz, Huiyan Huang and Wolfgang M. Sigmund. 2005. "Biocontinuous porosity in ceramics utilizing polymer spinodal phase separation." Journal of the European Ceramic Society. vol. 25. No. 6. Mar. 2005. pp. 883-889.

* cited by examiner

Figure 2 - Epoxy/PVA construct

A: Porous construct of merged PVA granules.

B: Formed epoxy disc with embedded PVA construct.

C: Exposed PVA granules after surface removal.

Figure 3 – Interconnected porous epoxy disc, 60x magnification.

Figure 4 – Merged PVA granules dissolved out of epoxy disc, 60x magnification.

METHOD OF PRODUCING INTERCONNECTED VOLUMETRIC POROSITY IN MATERIALS

CROSS REFERENCE TO RELATED APPLICATIONS

This application is a continuation of prior filed International Application, Serial Number PCT/US2006/041571 filed Oct. 23, 2006, which claims priority to U.S. provisional patent application No. 60/729,411 filed Oct. 21, 2005 which is hereby incorporated by reference into this disclosure.

FIELD OF INVENTION

This invention relates to the creation of porous materials. The method for creating pores within the materials allows control of volumetric arrangement of pores. The invention can be applied to but not limited to the creation of biomaterials for application in replacement and attachment procedures for hard and soft tissues.

BACKGROUND OF THE INVENTION

Metals are often used for hard tissue replacement such as bone. Illustrative metals used for implants include: stainless steel, titanium, chrome, and cobalt alloys. An osteoconductive environment must be established in a suitable bone replacement. The osteoconductive material provides scaffolding for cellular migration, cellular attachment, and cellular distribution. Bone will integrate into the osteoconductive material and secure the bone replacement. Metal implants often loosen at the interface with bone. Metal implants fail even when the surface of the implant is coated with an osteoconductive material. One reason for metal implant failure is the vastly different material properties compared to bone.

Carbon fiber reinforced carbon composites are also used as candidate bone replacement material because of their comparable rigidity to cortical bone. A comparison of bone rigidity to bone replacement material rigidity is insufficient to determine bone replacement suitability. A more detailed comparison of bone to the bone replacement material is needed to determine a suitable bone replacement. Material properties of ultimate strength, yield strength, and elastic modulus need to be compared between potential bone replacement materials and bone.

Soft tissue attachments to other soft and hard tissues can use resorbable and/or non resorbable materials. Materials such as silicon base elastomers and poly lactic acid are not currently formed with engineered and tailored volumetric porosity for in-growth of soft biological tissue or attachment to such tissue. Each tissue type has its own unique in-growth requirements. Those requirements include appropriate volumetric space and morphology.

What is needed is a suitable morphologically appropriate volumetric porosity for hard and soft tissue replacement and/or attachment material other than metal. Preferable materials possess three features:
1. the material is biocompatible and may have been used in previous biomedical applications such as joint prostheses, bone plates, dental posts, and long bone replacement; and
2. the material can be cast, allowing it to be fabricated into complex shapes.
3. the material's volumetric porosity is interconnected and capable of being arranged in a porosity gradient in one or more dimensions.

SUMMARY OF INVENTION

An illustrative embodiment of the invention includes a method of producing a porous construct. In the first step, a plurality of soluble particles are merged in the presence of a solvent; i.e. an inorganic acid such a phosphoric acid or a compound. The plurality of soluble particles in a preferred embodiment are in a container of the desired merged particle structure configuration. In one embodiment the compound comprises about 5% phosphoric acid and 95% distilled water. The plurality of soluble particles in a preferred embodiment are water soluble, such as PVA.

The soluble particles are then dried and a casting material, such as epoxy resin or other thermosetting epoxy, is added. Curing of the casting material and the plurality of soluble polymer particles results in a polymerized construct.

Once cured, the construct is sanded to expose the soluble particles. Once exposed, the soluble particles are dissolved away. In one embodiment, the soluble particles are dissolved in water between about 85 degrees Celsius and the $T_g°$ of the cross-linking polymer (150-170 degrees Celsius). Preferably the soluble particles are dissolved in a solvent, such as water, at a temperature below the $T_g°$ of the casting material.

The method can be enhanced by merging the plurality of soluble particles under pressure to increase the area of merged polymer particles. Further enhancements include curing the casting material and the plurality of soluble polymer particles in a vacuum chamber under about 23 in hg.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
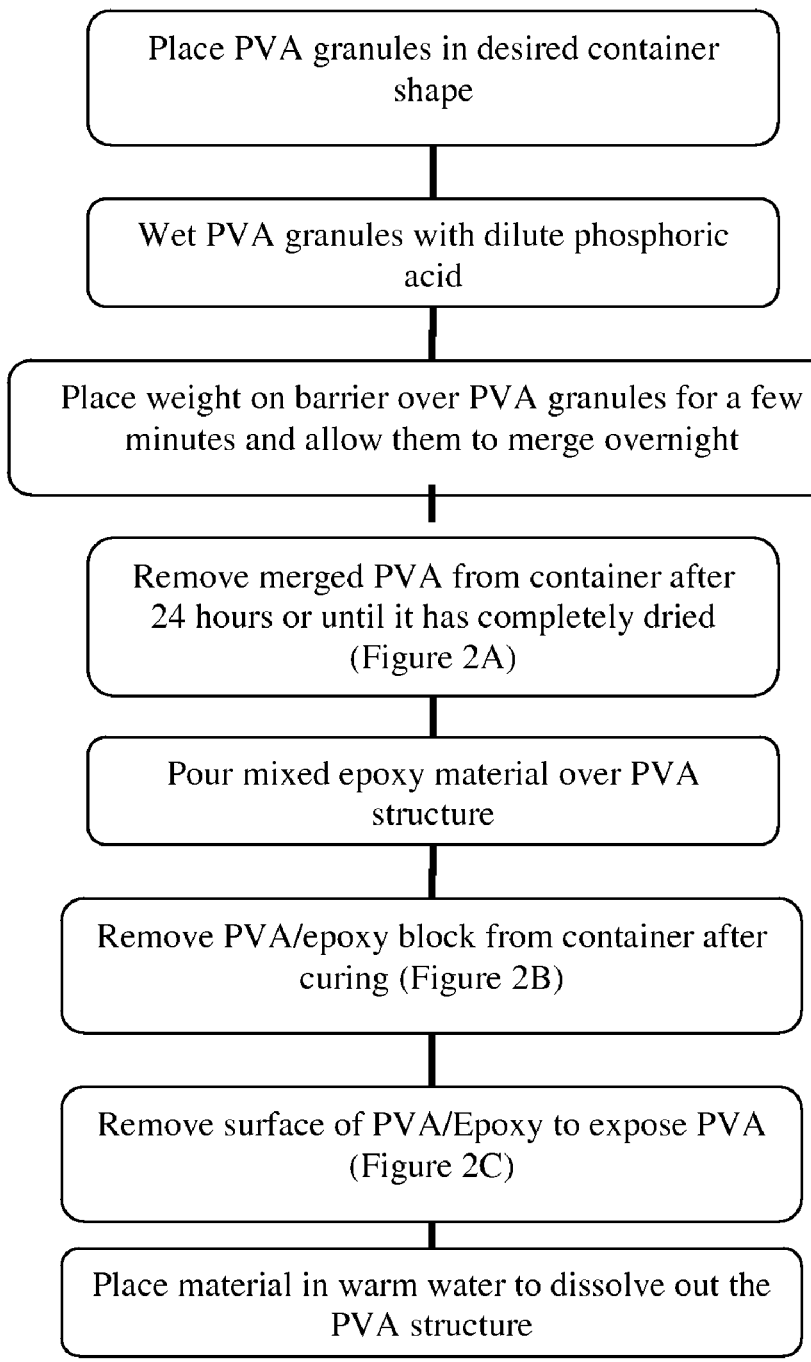
FIG. 1 is a process flow chart for creating volumetric porosity.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Bone Architecture

Porosity, apparent densities, and osteoconductive environment distinguish cortical and trabecular bone from one another. Cortical bone is defined as bone with less than 30% porosity (typically 5-10%). Porosity of trabecular bone is typically 50 to 90%. Pore sizes range from 50-450μm. Trabecular bone can be described architecturally as a bridging network of trabeculae forming a series of interconnected pores.

Apparent density of any solid is defined as the ratio of mass to bulk volume. Apparent density of human femoral cortical bone is in the range of 1.80 to 1.90 g/cm3. Apparent density of femoral trabecular bone is 0.20 g/cm3 to 0.40 g/cm3. Those values vary depending on the physical and inherited conditions of an individual. Osteoconductivity is described as a material property that supports tissue in-growth, osteoprogenitor cell growth and development for bone formation.

Osteoconduction is optimized by materials that mimic both bone structure and chemistry. Bone grafted from a donor (autograft) is regarded as the gold standard for bone replacement material. The primary determinate of the speed and completeness of osteoincorporation is the three dimensional structure of the implant. Osteoincorporation is described as the ability of bone to incorporate into the structure of a material. In order to achieve osteoincorporation three elements are necessary: 1) scaffolding for osteoconduction 2) growth factors for osteoinduction 3) and progenitor cells for osteogenesis. Osteoconduction is accomplished through structure similar to bone. Osteoinduction requires the proteins necessary to grow bone. Both elements are needed along with progenitor cells for osteointegration.

Porous structures with small interconnecting pores are more of a limiting factor for osteoconduction than actual pore size. Pore size and interconnectivity are critical factors affecting diffusion of nutrients, cell attachment, cell migration, and cell expression that are vital for bone formation. (LeGeros R Z: "Properties of osteoconductive biomaterials: calcium phosphates." Clinical Orthopedics, 395, 81-98, 2002; which is incorporated herein by reference). However, there is no consensus as to which pore size, shape, or interconnection promotes the best osteoconduction.

The combination of an osteoconductive matrix, an osteoinductive growth factor, and osteogenic cells may surpass the importance of graft material used. Any non toxic material can be used as long as it has an osteoconductive matrix, an osteoinductive growth factor, and osteogenic cells. (Vaccaro AR: "The role of the osteoconductive scaffold in the synthetic bone graft." Orthopedics, May 2002 supplement; which is incorporated herein by reference). Composite materials are used in the invention for the ability to tailor their mechanical properties and their light weight.

Soft Tissues are much like bone in that they are a hierarchal composite structure. Also like bone these tissues contain cells the produce proteins for growth and repair. Soft tissue growth, repair, and attachment to other soft or hard tissue require appropriate sized scaffold, proteins, and progenitor cells.

Composite Materials

A composite material, as previously mentioned, is one that consists of two or more constituents that are not soluble in each other. One of these constituents is referred to as the reinforcing phase, and the constituent in which it is embedded, is the matrix phase. The reinforcing phase is generally found in the form of fibers, particles, or flakes. Composite materials are used in many applications because of the high strength, toughness, and low weight. Strength of a material is defined as the applied load (force) point at which the material yields or fails. Toughness of a material is (MPa-m$^{1/2}$) the amount of resistance to crack growth.

Particle and fiber based composites were used in one embodiment of the invention. Particle based composites have hard particles surrounded by a softer matrix. Particle diameter is often only a few microns in diameter and comprises about 20 to 40 percent volume of the composite.

Particle reinforced composites have a large volume fraction of particle dispersed in the matrix. Load is shared by particles and the matrix. In the case of ZTA, fine zirconia particles are uniformly dispersed in an alumina matrix. Zirconia particles expand during firing and stress the alumina matrix, causing microcracks. Toughening is due to more energy required for crack growth around the higher elastic modulus zirconia particles.

Reinforcing fibers are made from short (discontinuous) or long (continuous) fibers. Fiber reinforced epoxy was used in an illustrative embodiment. Viscosity and flow rate can be adjusted in epoxy. Low viscosity epoxy allows wetting of the reinforcing phase and adhesion.

Fibers increase the elastic modulus of the matrix material. Increase in elastic modulus is due to the strong covalent bonds of the fibers to the matrix material. Strong covalent bonds increase the elastic modulus because bonds must be broken or moved to break or extend the fiber. The material properties of composite materials can be sufficient to mimic bone material properties. However, the main barrier in using composites as bone replacements is creating an optimal osteoconductive scaffold.

Creating a Porous Network (Epoxy)

Polymers are macromolecules consisting of different monomer length chains. Polymers are either formed by a chain-reaction polymerization or a step-reaction polymerization. Chain-reaction polymerization requires an initiator to start the expansion of the reaction. Once the reaction is initiated, the monomers link together to form a long chain. A reaction can be initiated by a free radical.

Different chain lengths give the polymer different molecular weights and consequently different properties. Those properties include resistance to chemicals, mechanical properties, melting point, and dissolution in specific solvents. A step-reaction polymerization, or condensation reaction, involves polymer chains growing by reactions that occur between two molecular species.

Creating a Porous Network (Dissolvable Polymers)

Non-toxic methods for creating porosity with dissolvable polymers such as poly(L-lactic acid) (PLLA), poly(L-lactic-co-glycolic acid) (PLGA), poly(glycolic acid) (PGA), and poly(vinyl alcohol) (PVA) were considered. Consideration was based on their current use in biological applications. Each of the polymers mentioned has been used in applications such as contact lenses, time released drug delivery, and dissolvable sutures.

Methods for producing a porous dissolvable polymer scaffold include: PGA non-woven mesh (fiber bonding), solvent casting/particulate-leaching, phase separation (emulsion), gas foaming (blowing).

Fiber bonding was one of the earliest designs in tissue engineering to create volumetric porosity. One of the first developed techniques consisted of immersing PGA fibers in a PLLA solution. The method was used to produce foam with porosities as high as 81%. Fiber bonding is undesirable due to its use of toxic solvents to achieve a PLLA solution.

Solvent casting/particulate-leaching involves mixing solid particles, such as sodium chloride, with a polymer solution and casting the mixture in a desired shape. Sodium chloride is dissolved from the mixture with water to produce a porous structure. Pore size and network extent are dependent on the sodium chloride particle size and weight fraction. Seventy weight percent and above of sodium chloride particles results in pores of high interconnectivity. Solvent casting/particulate-leaching method can require using undesired organic solvents and strong acids to attain a polymer solution. However, that method can be used to produce interconnected volumetric porosity the subject of this invention.

Polymers

PVA was used in an illustrative embodiment to create porosity in epoxy. PVA is a water soluble polymer of low toxicity. PVA is made up of repeating alcohol and acetate units. PVA is also available with different molecular weights of the parent poly vinyl acetate and different percent hydrolysis. Dissolution rate of polyvinyl alcohol in water varies accordingly. As the percent hydrolysis of the polymer increases, (increase in the alcoholic groups, decrease in the acetate groups), the temperature required to dissolve the polymer increases.

Epoxy is a thermosetting polymer that cures when mixed with a hardening agent. Thermoset polymers have covalent bonds cross-linking the polymer chains. Thermosets are insoluble in warm saline after cure.

i. EXAMPLE

The inventive method creates direct volumetric distribution of interconnected porosity in epoxy. Testing was done using epoxy (635 thin epoxy resin, 2:1 slow hardener, US Composites, West Palm Beach, Fla.) with no reinforcing components.

The methods of the prior art create a porous biodegradable polymer scaffold using a solvent merging/particulate leaching method (U.S. Pat. No. 6,436,426 which is incorporated herein by reference). The process begins by sieving the granular PLGA and sodium chloride particles to a particle size between 250-470 µm. Both of the particle species were then dry mixed together in different weight proportions. Ten grams of the combination were cast into a circular cylindrical Teflon© mold, 20 mm in diameter and 60 mm in height. The bottom of the mold was a stainless steel 180 µm mesh to contain the particle matter. Ten milliliters of organic solvent was then introduced to the mixture for 30 seconds. The solvent began to dissolve the surface of the PLGA particles. A vacuum pump was then attached to the apparatus to remove surplus solvent and coagulate the partially dissolved PLGA. One hundred milliliters of non-solvent was then passed through the composite to solidify and precipitate the PLGA. One thousand milliliters of distilled water was finally passed through the matrix under the same vacuum and the sodium chloride particles were dissolved out. Resulting samples were then dried under a 0.05 torr vacuum for 12 hours. Scanning electron microscopy, SEM, revealed a uniform pore distribution and well interconnected structure with a porosity of 87.7±5.6% and pore sizes of 343±126 µm. The process displayed potential for creating and controlling porous volumetric arrangement and pore size.

Here, PVA was chosen rather than PLGA in one embodiment to create porosity in the materials for its fast dissolving rate. No sodium chloride was used in the research to create the pores in the polymer. A mild phosphoric acid was used rather than an organic solvent. Organic solvent does not dissolve PVA. Residual organic solvent is not desired for biological applications.

A process flow chart for the method used to create interconnected porosity in epoxy is displayed in FIG. 1. 0.96 g of PVA granules were placed in a 25.4 mm cylindrical plastic container 25.4 mm in depth. PVA granules used were 125,000 molecular weight and 88 mole % hydrolyzed (Polysciences, Inc., Warrington, Pa.). Twenty drops of mild phosphoric acid compound, 5-6% phosphoric acid and 94-95% distilled water, wet the PVA granules. The PVA granules then adsorbed the mild phosphoric acid for five minutes. A 26 mm circular plastic separator, cut from a polyethylene sheet, was placed over the PVA granules. A 100 g weight was gently placed into the plastic container with the PVA granules. The weight remained on the PVA granules for 2 minutes to increase the area of PVA granules merged.

PVA construct was allowed to dry for 24 hours before it was removed from the plastic container. Twenty four hour duration of time allowed the PVA granules to dry, shrink, and merge, resulting in a porous construct of merged PVA granules. The dried PVA construct was then removed from the plastic cup. The plastic cup was coated with release agent. The PVA construct was then placed back into the plastic cup. A casting material of a mixed epoxy resin and hardener was poured over the PVA to fill the plastic container. The plastic container was then placed in a vacuum chamber under a 23 in hg vacuum for approximately 5 minutes. The "casting material" as used herein refers to any material that can be introduced into a mold, allowed to cure in the shape of the form, and then ejected to make a fabricated article.

Figure 2:
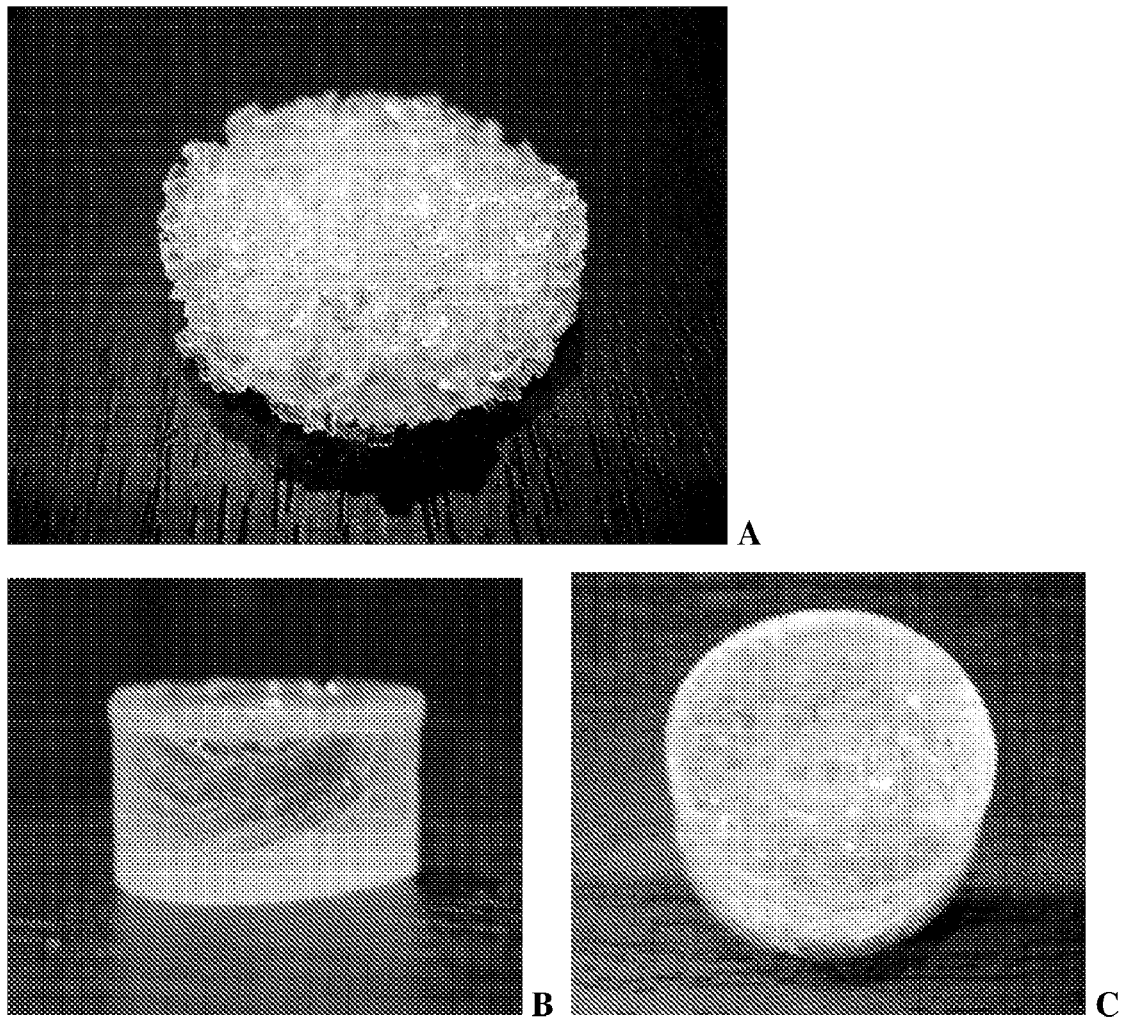
FIG. 2 Epoxy/PVA construct
A: Porous construct of merged PVA granules
B: Formed epoxy disc with embedded PVA construct
C: Exposed PVA granules after surface removal

After 48 hours curing time, the epoxy/PVA disc (FIG. 2B) was removed from the cup by percussion. In order to expose the PVA granules to the surface of the disc (FIG. 2C), the epoxy/PVA disc was sanded using 100 and 220 grit sandpaper sequentially in FIG. 8 motions. Epoxy/PVA disc was finally wet sanded with 600 grit sandpaper to achieve a smooth surface. Epoxy/PVA disc was next placed in warm water to dissolution the PVA from the disc. Water temperature was above the required temperature to dissolution PVA, 85° C., but below the $Tg°$ of the epoxy, 150-170° C. Dissolution of the PVA was done in warm water for 5-7 hours with periodic stirring of the water.

Porosity

Figure 3:
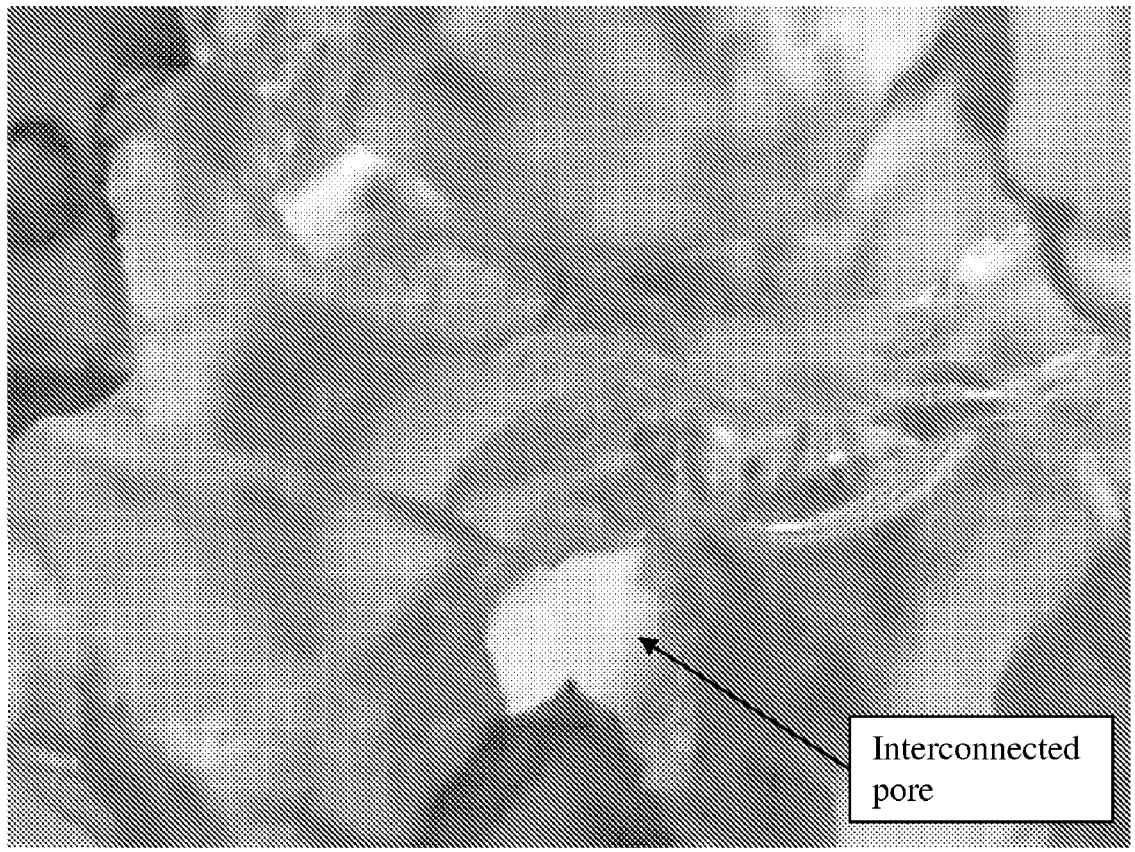
FIG. 3 is an image of an interconnected porous epoxy disc after PVA construct dissolved out, 60× magnification.
Figure 4:
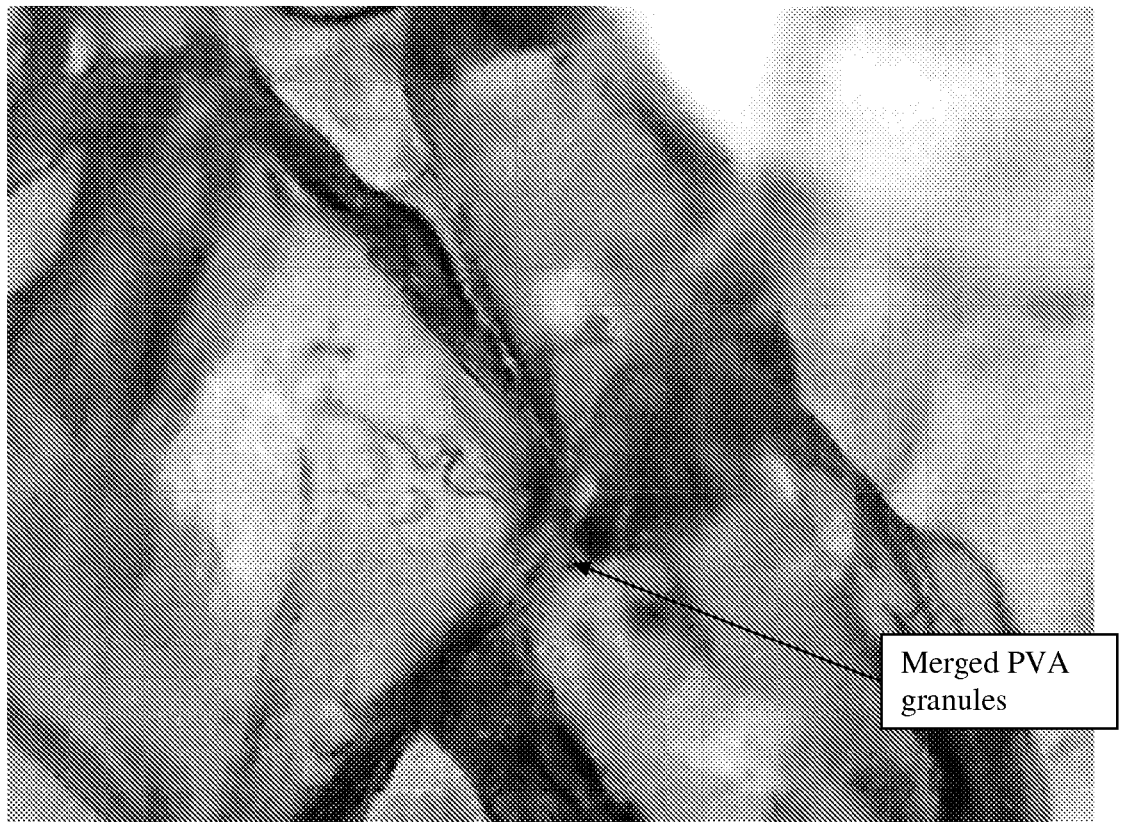
FIG. 4 is an image of the merged PVA particles.

Method used to create porosity produced a highly interconnected porous structure in the epoxy disc (FIG. 3). Those pores were representative of the PVA structure dissolved out. PVA particles were well merged (FIG. 4) and consequently easily dissolved out. Merging also made for a highly interconnected pore structure. Porosity line test revealed the structure to be 49% void space. Largest pore was 3.1 mm in length. The smallest pore was 0.21 mm in length. Those values were representative of the PVA granule size used in this example.

Determining an acceptable material to use as a bone replacement requires the consideration of several factors. Material properties of the bone substitute need to be sufficient enough to withstand everyday forces it is subjected to in a physiological environment. The bone substitute consequently must have similar material properties to bone. A mismatch in those material properties can lead to loosening at the bone replacement interface. Volumetric porosity must exist in the bone replacement for bone to incorporate into the bone replacement. A method to create and direct interconnected porosity in epoxy was established in this study. The method used to create interconnected porosity in epoxy also has potential to be used for fiber reinforced epoxy. For long-term considerations, the procedure to create such a bone replacement should be cost effective and time efficient without compromising quality.

The method used to create interconnected porosity for epoxy allows for control of the porous structure shape dissolved out of epoxy. Pore size can be controlled by the size of the PVA granules used to create the PVA construct. Area of porous epoxy also can be limited to the shape of the PVA construct. Shape of the PVA construct can be limited to the container used to merge the granules. Consequently, the method potentially allows for control of pore size and ability to limit the area of porous epoxy.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of producing a porous structure, comprising the steps of:
    merging a plurality of soluble particles in the presence of a solvent whereby the particles adhere to each other to form a porous construct of soluble particles;
    applying a non-soluble casting material to the merged soluble particles;
    curing the non-soluble casting material and the merged soluble particles;
    exposing the merged soluble particles; and
    dissolving the merged soluble particles to produce interconnected pores throughout at least a volumetric portion of the non-soluble casting material forming the porous structure wherein at least a subset of the pores are embedded within the non-soluble casting material.

2. The method of claim 1 wherein the plurality of soluble particles are water soluble.

3. The method of claim 2 wherein the soluble particles are dissolved at a temperature below the $T_g^\circ$ of the casting material.

4. The method of claim 3 wherein the $T_g^\circ$ of the casting material is above that of the solvent in which the soluble particles are dissolved.

5. The method of claim 1 wherein the plurality of soluble particles are merged in the presence of an inorganic acid.

6. The method of claim 5 wherein the inorganic acid is a phosphoric acid compound.

7. The method of claim 6 wherein the inorganic acid comprises about 5% phosphoric acid and about 95% water.

8. The method of claim 1 wherein the plurality of soluble particles are merged under external pressure.

9. The method of claim 1 wherein the casting material is a polymer.

10. The method of claim 9 wherein the polymer is a composition of epoxy resin, and a catalyzing agent.

11. The method of claim 1 wherein the casting material and the merged soluble particles are cured in a vacuum.

12. The method of claim 11 wherein the casting material and the merged soluble particles are cured in a vacuum of about 23 hg.

13. The method of claim 1 wherein the soluble particles are selected from the group consisting of poly(L-lactic acid) (PLLA), poly(L-lactic-co-glycolic acid) (PLGA), poly(glycolic acid) (PGA), and poly(vinyl alcohol) (PVA).

14. A method of producing an osteoconductive structure, comprising the steps of:
    merging a plurality of water soluble particles in the presence of an inorganic acid whereby the particles adhere to each other to form a porous construct of water soluble particles;
    drying the merged water soluble particles;
    applying a casting material to the merged water soluble particles;
    curing the casting material and the merged water soluble particles;
    exposing the water soluble particles; and
    dissolving the water soluble particles to produce interconnected pores throughout at least a volumetric portion of the non-soluble casting material forming the osteoconductive structure wherein at least a subset of the pores are embedded within the non-soluble casting material.

15. The method of claim 14 wherein the water soluble particles are dissolved in water at a temperature below the $T_g^\circ$ of the casting material.

16. The method of claim 15 wherein the $T_g^\circ$ of the casting material is above that of the solvent.

17. The method of claim 14 wherein the inorganic acid is a phosphoric acid compound.

18. The method of claim 17 wherein the inorganic acid comprises about 5% phosphoric acid and about 95% water.

19. The method of claim 14 wherein the plurality of water soluble particles are merged under external pressure.

20. The method of claim 14 wherein the casting material is a thermosetting epoxide polymer.

21. The method of claim 20 wherein the thermosetting epoxide polymer is a composition of epoxy resin and a catalyzing agent.

22. The method of claim 14 wherein the casting material and the merged soluble particles are cured in a vacuum.

23. The method of claim 22 wherein the casting material and the plurality of soluble particles are cured in a vacuum of about 23 hg.

24. A method of producing an osteoconductive structure, comprising the steps of:
    merging a plurality of water soluble polymer particles in the presence of a phosphoric acid compound;
    drying the plurality of water soluble polymer particles;
    applying a casting material to the plurality of water soluble polymer particles;
    curing the casting material and the plurality of water soluble polymer particles under about 23 in hg vacuum to create a polymerized construct;
    exposing the water soluble polymer particles; and
    dissolving the water soluble polymer particles in water at a temperature below $T_g^\circ$ of the casting material to produce pores throughout at least a volumetric portion of the osteoconductive structure wherein at least a subset of the pores are embedded within the non-soluble casting material.

25. The method of claim 1, further comprising merging a reinforcing phase with the plurality of soluble particles.

26. The method of claim 14, further comprising merging a reinforcing phase with the plurality of water soluble particles.

27. The method of claim 24, further comprising merging a reinforcing phase with the plurality of water soluble polymer particles.

* * * * *